(12) United States Patent
Kopenhaver Doheny et al.

(10) Patent No.: US 10,085,651 B2
(45) Date of Patent: Oct. 2, 2018

(54) METHODS FOR PREDICTING AND TREATING NECROTIZING ENTEROCOLITIS IN NEONATES

(71) Applicant: The Penn State Research Foundation, University Park, PA (US)

(72) Inventors: Kim Kopenhaver Doheny, Harrisburg, PA (US); Charles Palmer, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 989 days.

(21) Appl. No.: 14/383,787

(22) PCT Filed: Mar. 13, 2013

(86) PCT No.: PCT/US2013/030750
§ 371 (c)(1),
(2) Date: Sep. 8, 2014

(87) PCT Pub. No.: WO2013/138431
PCT Pub. Date: Sep. 19, 2013

(65) Prior Publication Data
US 2015/0094384 A1    Apr. 2, 2015

Related U.S. Application Data

(60) Provisional application No. 61/611,253, filed on Mar. 15, 2012.

(51) Int. Cl.
| | | |
|---|---|---|
| *A61B 5/024* | (2006.01) | |
| *A61B 5/08* | (2006.01) | |
| *A61B 5/00* | (2006.01) | |
| *G06F 19/00* | (2018.01) | |
| *A61B 5/0205* | (2006.01) | |

(52) U.S. Cl.
CPC ........ *A61B 5/0205* (2013.01); *A61B 5/02405* (2013.01); *A61B 5/0816* (2013.01); *A61B 5/4255* (2013.01); *A61B 5/7275* (2013.01)

(58) Field of Classification Search
None
See application file for complete search history.

(56) References Cited

U.S. PATENT DOCUMENTS

2005/0137484 A1    6/2005   Griffin et al.
2007/0254837 A1    11/2007   Hardin et al.

FOREIGN PATENT DOCUMENTS

WO      2011053832 A1    5/2011

OTHER PUBLICATIONS

International Search Report and Written Opinion for PCT/US2013/030750 dated May 17, 2013.
Porges, "The polyvagal theory: New insights into adaptive reactions of the autonomic nervous system." Cleveland Clinic Journal of Medicine, 76(2):86-90, Apr. 2009.
Veerappan et al. "Spectral Analysis of Heart Rate Variability in Premature Infants with Feeding Bradycardia." Pediatric Research, vol. 47, pp. 659-662, 1999.

*Primary Examiner* — Lori A. Clow
(74) *Attorney, Agent, or Firm* — Buchanan Ingersoll & Rooney PC

(57) ABSTRACT

Embodiments are presented herein that provide early prediction of the development of necrotizing enterocolitis by a preterm infant through analysis of the high frequency component of heart rate variability, optionally with analysis of respiration rate. Methods of treatment following prediction area also reported.

14 Claims, 5 Drawing Sheets

Comparison between infants with NEC versus those infants without NEC:   ** p = 0.001

METHODS FOR PREDICTING AND TREATING NECROTIZING ENTEROCOLITIS IN NEONATES

CROSS-REFERENCE TO RELATED APPLICATIONS

This application claims priority to U.S. Provisional Patent Application No. 61/611,253, filed on Mar. 15, 2012, and incorporated by reference herein.

BACKGROUND OF THE INVENTION

Field of the Invention

Embodiments of the invention relate to methods for the early identification of a subset of newborn infants at risk for developing necrotizing enterocolitis using analysis of the high frequency component of heart rate variability.

Description of the Related Art

Necrotizing enterocolitis (NEC) is a common and often devastating gastrointestinal disorder that primarily afflicts preterm infants. NEC occurs when pathogenic organisms produce inflammation, injury, and intramural gas in a preterm infant. Approximately 6-10% of preterm infants below 1500 g birth weight are afflicted with NEC. The annual cost of managing NEC and its long term consequences on the compromised bowel are measured in the billions of dollars. NEC is a major clinical problem for every neonatal intensive care unit that cares for preterm infants.

Success of treatment for NEC requires early diagnosis. Early diagnosis will be facilitated by knowing days in advance which subset of newborn infants are at increased risk so surveillance can be enhanced or effective intervention started. Unfortunately, there are currently no ways of screening infants early in their hospital stay for the risk of developing NEC.

BRIEF SUMMARY OF THE INVENTION

Embodiments of the invention provide methods for determining that a patient is at an elevated risk for developing necrotizing enterocolitis. These methods may include, for example, the steps of monitoring a patient's heart rate to determine heart rate variability, wherein the heart rate variability having a high frequency component; analyzing the high frequency component of heart rate variability to determine power of the high frequency component; and, when the power of the high frequency component is less than 8 msec$^2$, preferably less than 5 msec$^2$, determining that the patient has an elevated risk for developing necrotizing enterocolitis relative to a patient who has a heart rate variability with a high frequency component having a power greater than 8 msec$^2$, preferably greater than 5 msec$^2$.

In some embodiments the patient is a preterm neonate with a mass less than or equal to 1500 g, and in others less than or equal to 3000 g. In further embodiments the monitoring step is conducted between 5 and 8 days after birth of the patient. In further embodiments the elevated risk is indicative of development of necrotizing enterocolitis within 12 hours to 30 days of a determination of risk.

A further preferred embodiment includes a method for determining that a patient is at an elevated risk for developing necrotizing enterocolitis, comprising the steps of monitoring a patient's heart rate to determine heart rate variability, where the heart rate variability having a high frequency component; monitoring the patient's breathing rate; calculating a high frequency range within which the patient is at an elevated risk for developing necrotizing enterocolitis, wherein said high frequency range is calculated by dividing the range of the monitored breathing rate by 60, determining the mean breathing rate, and setting a range that incorporates a measure of the variance on either side of the mean. For example, one embodiment uses the mean±2 Standard Deviations (SD). The mean breathing rate may be set for an individual patient or be a mean that has been created from data obtained from a number of patients. This may include analyzing the high frequency component of heart rate variability to if the power of the high frequency component falls within the calculated high frequency range; and when the power of the high frequency component falls within the calculated high frequency range, determining that the patient has an elevated risk for developing necrotizing enterocolitis relative to a second patient who has a heart rate variability with a high frequency component that does not fall within a second high frequency range calculated based on the second patient's breathing rate.

Another embodiment includes a method for treating a patient for necrotizing enterocolitis, comprising monitoring a patient's heart rate to determine heart rate variability, said heart rate variability having a high frequency component; analyzing the high frequency component of heart rate variability to determine power of the high frequency component; when the power of the high frequency component is less than 8 msec$^2$, determining that the patient has an elevated risk for developing necrotizing enterocolitis relative to a patient who has a heart rate variability with a high frequency component having a power greater than 8 msec$^2$; and, if the patient has been determined to have a high risk of developing necrotizing enterocolitis, administering to the patient a treatment effective to lessen or eliminate at least one of necrotizing enterocolitis or the elevated risk of developing necrotizing enterocolitis.

Other details, objects, and advantages of the invention will become apparent as the following description of certain present preferred embodiments thereof proceeds.

DETAILED DESCRIPTION OF THE FIGURES

Figure 5:
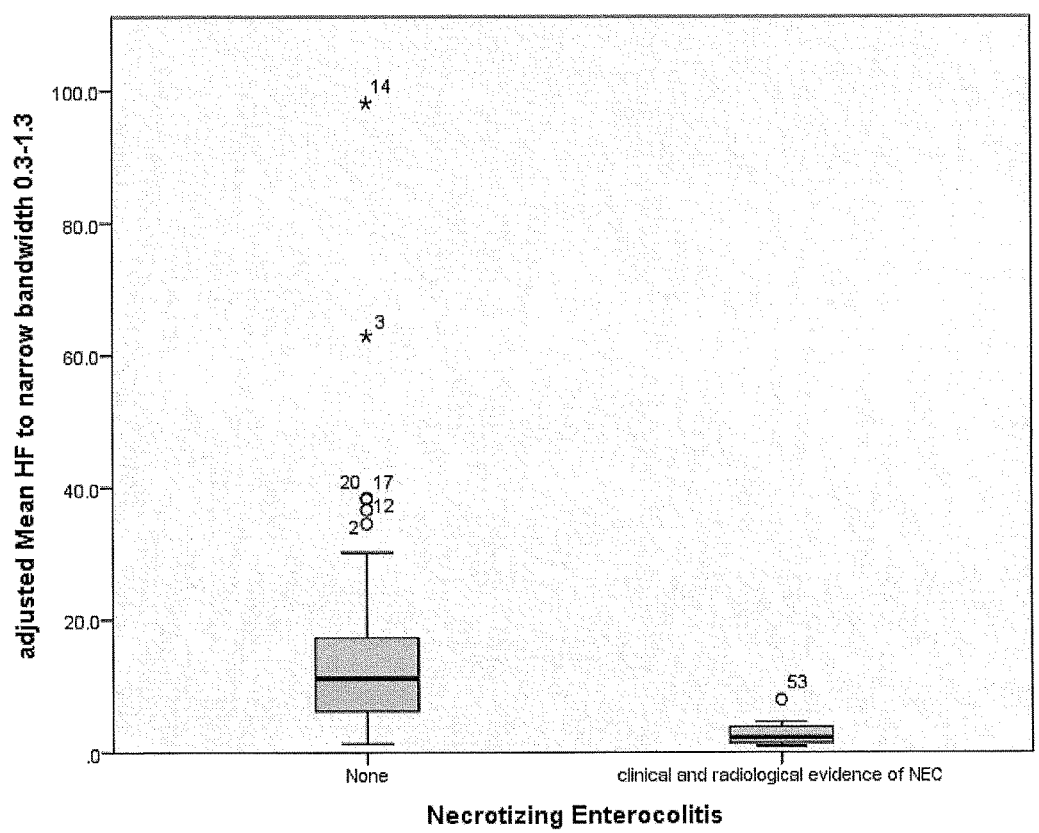

FIG. 5 shows a Box and Whisker plot of a group from Example 3 that did not get NEC ("None") and a group that later developed NEC. The Y axis shows the HF power measurement using the frequency range of 0.3-1.3 Hz. The groups are statistically different p<0.0001 Mann Whitney U, as discussed in Example 3.

DETAILED DESCRIPTION OF THE INVENTION

We have found that measurements of the high frequency component of heart rate variability may be used to identify a subset of patients who are likely to develop NEC. This identification allows application of prophylactic treatment to either prevent or lessen the effects of the onset of NEC. This may also allow medical professionals to increase other diagnostic tests for NEC when they become available. It may also permit medical professionals to identify a high risk group (subset) for clinical trials that involve modalities to treat or prevent NEC. Typical patients of interest are infants born before a gestational age of 37 weeks and/or with a birth weight of less than 3000 g, sometimes less than 2500 g, and sometimes less than 1500 g.

The activity of the vagus nerve may be measured by a kind of heart rate variability (HRV) known as frequency domain analysis. The high frequency (HF) component of HRV is influenced by the parasympathetic branch of the autonomic nervous system. Vagal nerve innervation provides most of the parasympathetic activity, Vagal nerve innervation of the heart is influenced by breathing rate and effort. This is termed sinus respiratory arrhythmia. Gastrointestinal (GI) motility is stimulated by vagal nerve impulses. Secretion and blood flow are also mediated by the vagus nerve. Normal GI motility is important to prevent stasis and overgrowth of pathogenic bacteria.

Typically the HF component of HRV is found in the 0.2 to 2.0 Hz bandwidth. There is some evidence to suggest that individualizing the HF bandwidth to the infant's individual breathing rate may be beneficial in assuring that the peak HF power is captured in the area under the curve measurement. In one sample of 53 preterm infant subjects, the mean observed respiratory rate at rest was 30-82 breaths per minute. Thus, the specified HF bandwidth for this sample was 0.3-1.3 Hz.

Embodiments of the invention use respiration to locate the most appropriate frequency band of parasympathetic activity in the HRV signal. This results in isolation it from the effects of the sympathetic aspect of the autonomic nervous system. Spontaneous breathing and the respiratory rate influence vagal nerve activity. Vagal nerve activity is the major contributor to the HF component that is measured. For example, some texts indicate the high frequency (HF) ranges is between 0.15 to 0.4 Hz; however newborn infants in at least one study breathe at an average rate of 50 br/min. If one allows two standard deviations (30 br/m) on either side of the average rate, the range is 20-80 br/m. Expressing this as Hz, the frequency band for calculating HF power becomes 0.3-1.3 Hz. Note the spread between 0.3 and 1.3 Hz in this embodiment is 1 Hz.

In a preferred embodiment each patient's individual breathing rate is used to calculate the HF range for measuring power. Where the spread differs from 1 Hz it should be normalized to 1 HZ for the purpose of comparison. The power measurement is also dependent on the duration of analysis and will increase with longer sampling periods. In a preferred embodiment reflected in the examples reported herein, the measurement was sampled for 120 s. Hence, the sampling interval also should be standardized the sake of comparison between patients. When providing a cut-off value for HF, power will change with the duration of sampling and with the HF range analyzed. In a preferred embodiment the value is 8 $msec^2$. In a more preferred embodiment it is 5 $msec^2$.

Although prior studies have examined HRV or HF, none have appreciated the importance of the HF component to the early diagnosis and treatment of NEC. See, for example, Moorman, et al., "Mortality Reduction by Heart Rate Characteristic Monitoring in Very Low Birth Weight Neonates: A Randomized Trial" *J. Peds.* 2011; Diego, et al., "Preterm Infant Massage Elicits Consistent Increases in Vagal Activity and Gastric Motility That Are Associated With Greater Weight Gain" *Acta Paediatrica* 2007 96: 1588-1591; U.S. Pat. No. 4,510,944, to Porges; and U.S. Pat. No. 6,216,032, to Griffin, et al.

The ability to have early identification and treatment will allow patients to be consistently and meaningfully monitored for potential NEC, for example, through the use of a bedside monitor. This may be done by monitoring the patient's heart rate and respiratory rate (for example, through an electrocardiogram, and impedance changes in chest movement respectively), and subjecting the results to HRV and HF analysis. Modern bedside monitors have computing power built in and should be able to perform this function in the background and provide the clinician with an HF power score. Depending on the specific parameters of the analysis and risk assignment (i.e. duration of sampling and frequency range), further analysis or treatment of a patient may be warranted.

In preferred embodiments of the invention the timing of the baseline measurement in the first week of life (postnatal days 5-8) represents a critical window that is a period of time when HF measurement is most representative of the individual's stress and innate immune response ability. In preferred embodiments the approach of standard measurement of HF to reflect parasympathetic tone is obtained during a resting, light sleep state and at 30-50 minutes post-feeding (i.e. post-prandially). Results indicate that the measurement done on days 5-8 is predictive of risk for the next 2-3 weeks. Because predictive ability may wane the farther out in time one is from the original assessment, in some embodiments a the measurement is repeated on a weekly or biweekly interval.

Although not wishing to be bound by theory, the inventors believe that the HF component of HRV reflects susceptibility to NEC at least in part because HF reflects low parasympathetic tone and low vagal tone. Low parasympathetic tone, in turn, is associated with diminished gastrointestinal motility and a dampened cholinergic anti-inflammatory response.

Typically, a resting HF showing significantly lower power ($<8$ $msec^2$, preferably $<5$ $msec^2$) is reflective of low parasympathetic tone and indicative of a morbidity risk, and increased likelihood of developing NEC. The results in Table 3 of the experimental data (below) show that for observed NEC in at least one trial, the overall percentage of cases predicted correctly was 93.3%. Sensitivity, which is the proportion of correctly classified cases of NEC predicted by low HF, was 100%. Specificity, the proportion of cases predicted by HF to remain free of NEC (i.e., remain well) during hospitalization was 91.3%. There were no false negatives. The false positive rate was 2/2+7 or 22%. It is important to recognize that there is a relationship between low HF power and the ability to set a low level for allocating infants into the high risk subset. The particular level will depend on how the analysis was done. In our study using the narrowed HF range of 0.3-1.3

Hz for analysis, a HF power below 5 $msec^2$ identified all the patients who developed NEC.

Although we have found that measurement of parasympathetic tone alone may be helpful in predicting NEC, we have also found that the utility of the measurement as a predictor for NEC may be enhanced by individualizing the spectral bandwidth for parasympathetic tone measurement by reviewing the association of breathing rate and effort. For example, when the breathing rate of an individual baby (Mean±2 SD) is 20-80 breaths per minute, the bandwidth range, in Hz, of the relevant vagal tone may be 20/60-80/60, or 0.3-1.33 Hz. In another embodiment one could just assume a breathing rate that would include most babies in a given age bracket. For preterm infants for example a breathing range of 20-80 would be relevant but variations around that rate would also be effective, for example 30-90 br/min or 30-70 br/min. In a preferred embodiment one uses the patient's own rate and calculates the HF frequency range from that.

In other embodiments the HRV analysis may be further refined by using a patient's actual respiratory rate measured during HRV data collection to the set the HF range for analysis.

It should also be emphasized that while many of the preferred embodiments state that allocation of a patient to a high-risk subset is dependent on analysis of that patient's HF power as more than one standard deviation or more than two standard deviations below the mean HF power for preterm infants, other embodiments of the invention contemplate use of other "below the mean" measurements as indicative of a patient being in a high-risk subset for development of NEC. For example, some practitioners may decide that any patient with any HF power below the mean bears further examination and/or treatment. In other cases a practitioner may decide to limit further inquiry and treatment to those preterm infants whose HF power falls below multiples of the standard deviation greater than two, for example three or even four or more standard deviations below the mean.

In some embodiments, HF analysis of potential NEC is most predictive if performed within 5-8 days of a patient's birth. In other embodiments it is most effective if performed within 4-8 days of birth. Detection of low HF power may occur, for example, from 12 hours to 20 days prior to confirmation of diagnosis of NEC. HF analysis of HF power for the potential for developing NEC can be performed later than 8 days to extend the prediction interval.

Once a likelihood of developing NEC has been identified, measures may be taken to prevent NEC or lessen NEC's effects. For example, additional antibiotics may be administered. To attempt to prevent NEC or detect it early one can prefer to use breast milk feedings, use probiotics, and investigate early signs of NEC with increased suspicion including evaluation of stool for blood and radiological investigations of the intestine. Enteral feedings could be held and antibiotics given at the first sign of clinical NEC.

Embodiments of the invention may be further understood by reference to examples, as reported below.

Example 1

In one study thirty preterm infants (born at 29-36 weeks gestational age) were enrolled in a prospective, observational study. Infants were excluded if they had congenital anomalies, central nervous system lesions, or if they required ventilation at the time of enrollment. On day 5-7 of life resting HRV was measured postprandially and analyzed using power spectral analysis. HRV measures were obtained from the analog output of the ECG using HRV acquisition software. We performed a frequency domain analysis and selected the high frequency (HF) band (0.2-2 Hz) specifically because the HF band corresponds to parasympathetic or vagal activity. Infant health outcomes for the first month of life were obtained by chart audit by coders blinded to the HRV analysis.

Figure 1:
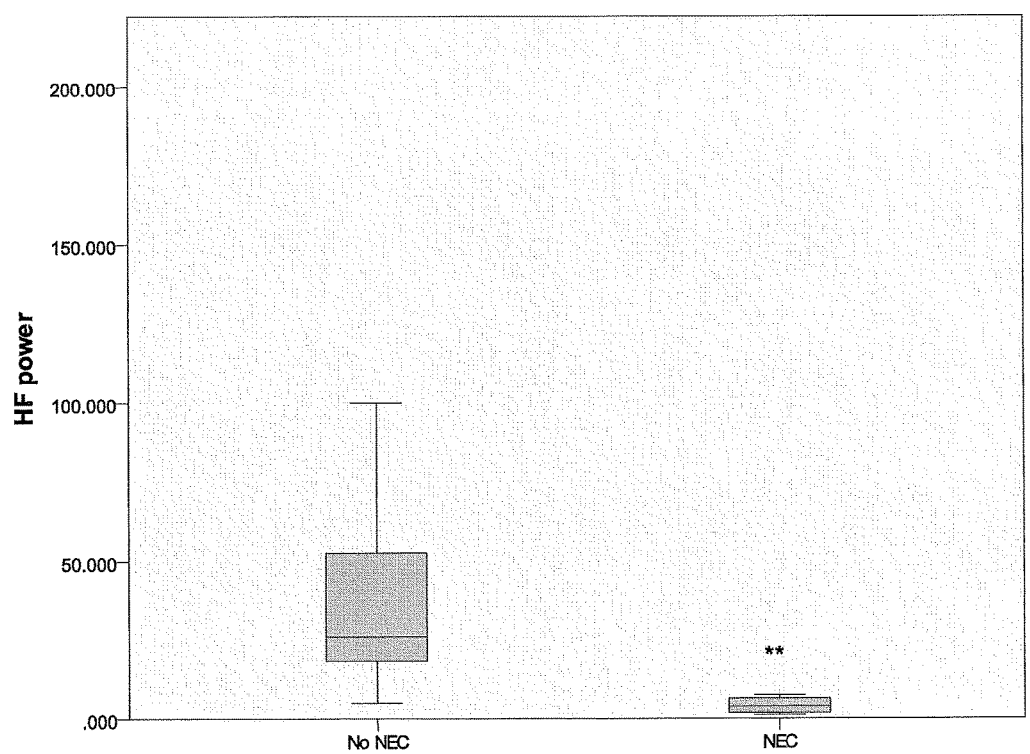
FIG. 1 shows results of the study described in Example 1.

The 30 enrolled subjects were 32.6±1.5 wks ga (mean±SD) and weighed 1878±409 gms. Four (13%) of the 30 study infants developed NEC confirmed by radiologic (*pneumatosis intestinalis*) and clinical findings. Seven infants treated for sepsis within the first 10 days of life were excluded from the analysis as our focus for this study was on NEC. 19 infants who remained healthy for the first month of life were compared to those infants with confirmed NEC. NEC infants had significantly lower power in the HF band, 2.8±1.4 msec$^2$ (mean±SE) compared to the healthy infants, 45±10 msec$^2$, P=0.001. This is an example of normal values for this population. Interestingly, the detection of the low HF power was obtained from 12 hrs to 9 days prior to the confirmatory diagnosis of NEC. Results are shown in FIG. 1.

Although not analyzed here, we also note that vagal tone to the spleen, which is innervated by the intestinal branches of the vagus, has an antiinflammatory action on the body.

Example 2

An additional 23 infants were examined and the resulting data incorporated into the results described in Example 1, further confirming the results.

Example 2 reports:

A description of our study design and methods

Presentation and discussion of research findings (N=53) using heart rate variability as a biomarker for NEC prediction in healthy preterm infants, compare group mean statistics between healthy infants who remain healthy vs. those who go on to develop NEC post measurement Discussion of a critical value of HF in healthy preterm infants in the first week of life to be used as a clinical index for NEC vulnerability Discussion of results of our first pilot cohort using HF power to predict combined outcomes of NEC and late-onset sepsis Methods: In a prospective cohort study of 53 healthy, non-ventilated preterm (28-35.2 wks PMA; M+SD=32.1±1.7) infants 9/53 (17%) developed Bell's stage IIa+ necrotizing enterocolitis (NEC). Heart rate variability (HRV) was measured on day 5-8 of life when the infants were not acutely ill. HRV was analyzed using spectral analysis. The high-frequency (HF) component was measured at a bandwidth of 0.2-2 m/sec$^2$. Chart audit data was kept throughout the infant subjects' hospital course. The timing and diagnosis of NEC (determined by clinical and radiologic evidence of NEC) ranged between 12 hours and 20 days after the HF measurement and prior to the onset of clinical symptoms of illness. The median interval from HF measurement to onset of NEC was approximately 6 days.

TABLE 1

Independent Samples Test

| | Levene's Test for Equality of Variances | | t-test for Equality of Means | | | | | | |
|---|---|---|---|---|---|---|---|---|---|
| | | | | | | | | 95% Confidence Interval of the Difference | |
| | F | Sig. | t | df | Sig. (2-tailed) | Mean Difference | Std. Error Difference | Lower | Upper |
| Equal variances assumed | 5.023 | .029 | 2.030 | 51 | .048 | 23.819164 | 11.735786 | .258591 | 47.379737 |
| Equal variances not assumed | | | 4.466 | 45.127 | .000 | 23.819164 | 5.333051 | 13.078685 | 34.559644 |

Results: An independent samples comparison of mean HF power between NEC and non-NEC groups was done. Statistical analysis was done using SPSS version 19.0. All tests were 2-sided and considered significant if P<0.05. Table 1 indicates that the difference in HF power between groups is 23.8 (95% CI 0.26-47.37) P=0.048.

Figure 2:
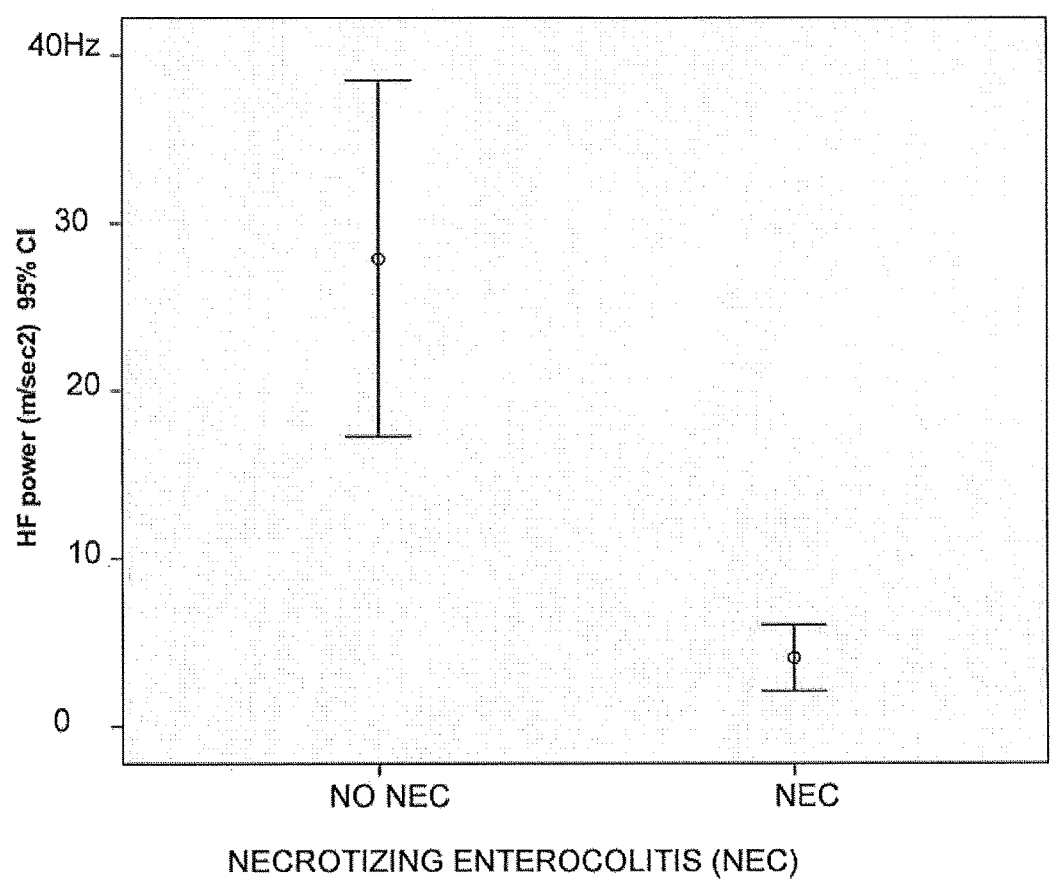
FIGS. 2 and 3 show results of the study described in Example 2.

A Kruskal-Wallis non-parametric test showed differences of the HF power value between groups to be significant at P<0.001. (FIG. 2) There was an inverse relationship between HF power and NEC, such that those infants with HF power below 8 msec2 all developed NEC. Identifying a critical value for risk identification is clinically most relevant and is akin to the value needed for a positive test. The specific critical value will depend on how the HF analysis is performed related to the adjusted frequency of the HF bandwidth, duration of sample signal acquisition (120 sec epochs) and timing of the sampling frequency (1000 s/sec). In addition, the measurements of HRV related to sleep state and feeding are important confounding variables which must be controlled. In our study we collected HRV data in the afternoons at 30-50 min post-feeding/handling while infants were in a light sleep state. Validity of data was assured through obtaining 30-45 minutes of continuous data and screening data epochs to remove movement artifacts and/or ectopic beats. We sampled for 120 s using the bandwidth of 0.2-2.0 Hz.

Further analysis of the data using a binary logistic regression model fitted to a point estimate at 95% confidence interval for the dichotomous variable of NEC Vs Non-NEC (1 and 0) showed an odds ratio of 0.67; 95 CI=0.488-0.914; P=0.012, Beta=−0.40. The model was determined to have good fit, Nagelkerke R2=0.54, and Hosmer Lemeshow test Chi Square=0.78; P=0.99.

TABLE 2

Logistic Regression was used to identify sensitivity/specificity of HF power to predict NEC

| | | | Predicted | | |
|---|---|---|---|---|---|
| | | | Necrotizing Enterocolitis | | |
| | Observed | | None | clinical and radiological evidence of NEC | Percentage Correct |
| Step 1 | Necrotizing Enterocolitis | None | 41 | 3 | 93.2 |
| | | clinical and radiological evidence of NEC | 5 | 4 | 44.4 |
| | Overall Percentage | | | | 84.9 |

| | | | Predicted | | |
|---|---|---|---|---|---|
| | | | Necrotizing Enterocolitis | | |
| | Observed | | None | clinical and radiological evidence of NEC | Percentage Correct |
| Step 1 | Necrotizing Enterocolitis | None | 41 | 3 | 93.2 |
| | | clinical and radiological evidence of NEC | 5 | 4 | 44.4 |

TABLE 2-continued

Logistic Regression was used to identify sensitivity/specificity of HF power to predict NEC

| Overall Percentage | 84.9 |
|---|---|

The results for predicted vs. observed (i.e. have clinical disease) Non-NEC and NEC cases, show the overall percentage of cases predicted correctly was 84.9%. Sensitivity, the proportion of NEC cases predicted by low HF who had diagnostically proven NEC was 44.4%. Specificity, the proportion of correctly classified non-NEC cases predicted by HF who remained free of NEC during hospitalization was 93.2%. The false negative rate was 5/41+5 or 10.8%. The false positive rate was 3/3+4 or 42.8%.

The analysis shows that all patients who were going to develop NEC could be identified some days in advance of clinical disease if they fell below the cut of HF power level of 8 msec2. While being 100% sensitive, this cut-off value provided a false positive rate of 42.8%. We examined the first 30 patients in which we had more complete data for other clinically relevant morbidities other than NEC. Specifically we looked for late onset clinical sepsis (sepsis after 72 hrs). The patients with clinical sepsis received a course of antibiotics for presumed sepsis because they were clinically ill but did not have a confirmed blood culture.

In the initial pilot cohort study of 30 subjects (discussed in Example 1), several infant subjects became ill with sepsis after 10 days of age. Thus, a model for analysis was created combining the outcomes of NEC and sepsis. A binary logistic regression model fitted to a point estimate at 95% confidence interval for the dichotomous variable of NEC or late-onset sepsis was created with a dichotomous outcome variable coded as NEC or Clinical Infection (1) Vs Healthy (0) subjects. Comparison between groups was significant at p<0.001 (See FIG. 3).

Figure 3:
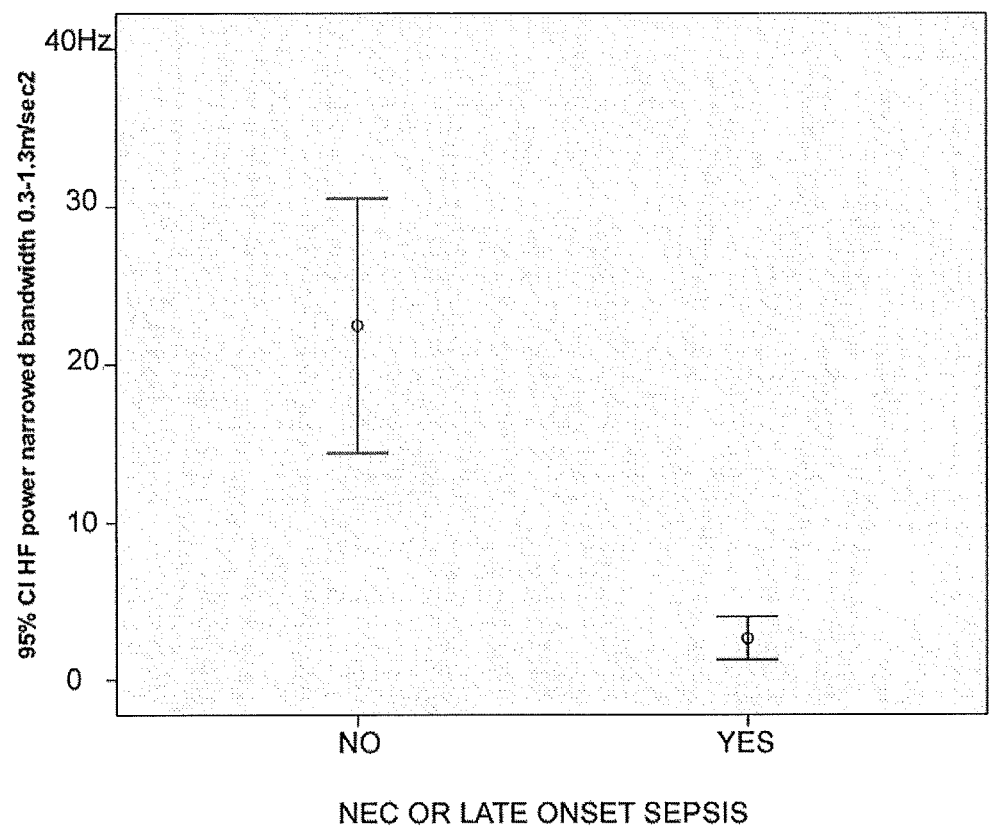

Note, for this analysis we chose to narrow the bandwidth analyzed to reflect the range of breath rates we observed in the 30 patients. The rationale for doing this is that the parasympathetic tone is influenced by the respiration (Aysin & Aysin, 2006). The average breath rate was 50 br/m. We chose to include 2 standard deviations (30 br) on either side of the mean i.e. 20-80 breaths and expressed this rate in terms of Hz to identify the bandwidth used for analysis. This came to a narrowed bandwidth of 0.3-1.3 Hz (FIG. 3).

TABLE 3

Logistic Regression was used to identify sensitivity/specificity of HF power to predict NEC or late-onset infection

| | | | Predicted | | |
|---|---|---|---|---|---|
| | | | NEC or clinical infection after 10 days | | Percentage |
| | Observed | | none | yes | Correct |
| Step 1 | NEC or clinical infection after 10 days | none | 21 | 2 | 91.3 |
| | | yes | 0 | 7 | 100.0 |
| | Overall Percentage | | | | 93.3 |

The results in Table 3 show for observed NEC or late clinical sepsis, the overall percentage of cases predicted correctly was 93.3%. Sensitivity, the proportion of correctly classified cases of NEC or late sepsis predicted by low HF was 100%. Specificity, the proportion of cases predicted by HF to remain free of NEC or late-onset sepsis (i.e., remain well) during hospitalization was 91.3%. There were no false negatives. The false positive rate was 2/2+7 or 22%.

Example 3

Example 3 reports a combined analysis of two further studies using HRV to predict nectrotizing enterocolitis. Descriptive statistics of the 70 subjects are shown in Table 4:

TABLE 4

Descriptive Statistics of Test Subjects

| | N | Minimum | Maximum | Mean | Std. Deviation |
|---|---|---|---|---|---|
| Male Gender | 70 | 0 | 1 | .51 | |
| SNAP- (score for neonatal acute physiology) | 70 | 0 | 9.0 | 3.029 | 2.0070 |
| Gestational Age | 70 | 28.0 | 35.2 | 31.923 | 1.7890 |
| Birth weight in grams | 70 | 1070 | 2803 | 1791.10 | 419.222 |

For each of these subjects we determined an adjusted mean HF power at a bandwidth between 0.3 and 1.3 Hz between the $5^{th}$ and $8^{th}$ day of life. The results were divided into those that did not develop NEC (listed as "None") and those that developed NEC. Results are shown in Table 6, below. On average the development occurred about two weeks after the measurement of HF power. Results are presented in an ROC Curve shown as FIG. 4, in a summary in Table 7, and in an area under the curve analysis in Table 8.

TABLE 6

Adjusted Mean HF Power at bandwidth 0.3-1.3 Hz

| Necrotizing Enterocolitis | Mean Power (msec2) | Std. Deviation |
|---|---|---|
| None | 15.012 | 15.4778 |
| Clinical and radiological evidence of NEC | 3.073 | 2.2138 |
| Total | 13.477 | 15.0028 |

TABLE 7

Table 7: Validity of HF power as a Screening Tool for NEC

| | NEC | No NEC | |
|---|---|---|---|
| HF power < 4.68 msec$^2$ | 8 | 8 | 16 |
| HF power > 4.68 msec$^2$ | 1 | 53 | 54 |
| Total | 9 | 61 | 70 |

Sensitivity = 88.9%
Specificity = 86.9%
Positive Predictive value = 50%
Negative Predictive Value = 98.1%

TABLE 8

Figure 4:
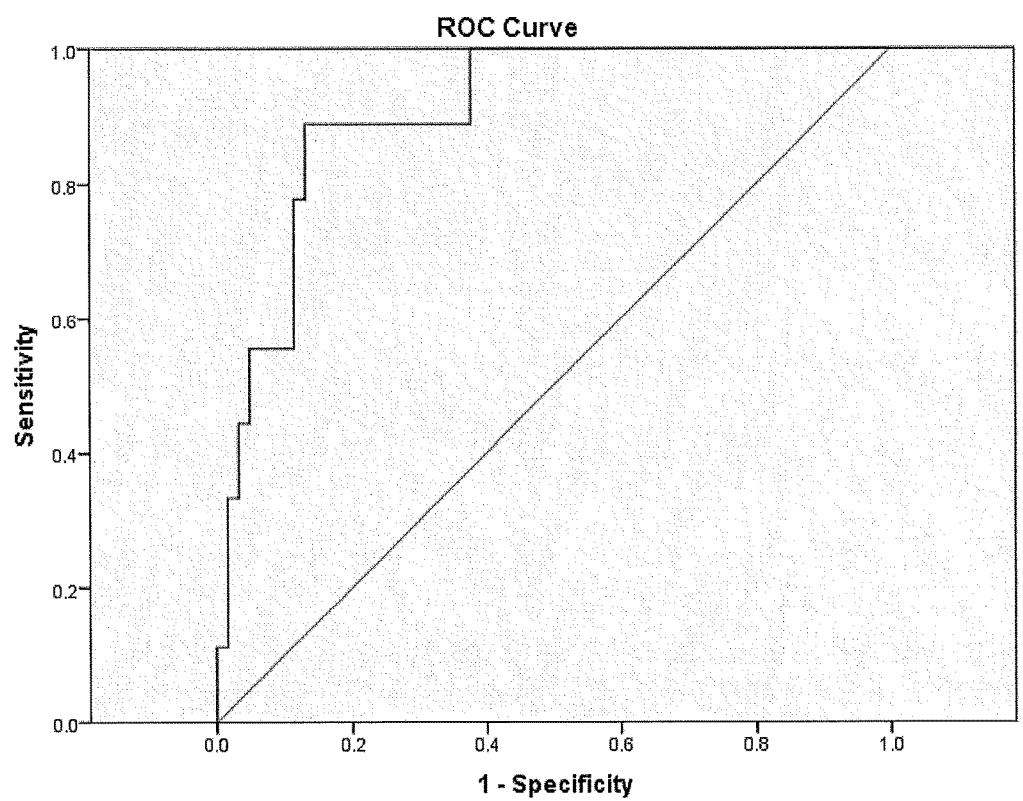
FIG. 4 shows an ROC curve for sensitivity and specificity of an study described in Example 3.

Area Under the Curve for FIG. 4
Test Result Variable(s): adjusted Mean
HF Power to narrow bandwidth 0.3-1.3

| Area | Std. Error[a] | Asymptotic Sig.[b] | Asymptotic 95% Confidence Interval | |
|---|---|---|---|---|
| | | | Lower Bound | Upper Bound |
| .905 | .044 | .000 | .818 | .992 |

[a]Under the nonparametric assumption

We further prepared a box and whisker plot to compare the group that did not get NEC (shown as "None") with the group that did. The Y axis of the graph, included as FIG. 5, shows the HF power measurement using the frequency range of 0.3-1.3 Hz. The groups are statistically different with a value of p<0.0001 according to the Mann-Whitney U test.

Discussion: These data support the claimed invention, demonstrating that HF power measurement, which is considered a measure of parasympathetic system tone, reflects the individual state of vulnerability—or potential that increased stress load will result in clinical illness. Several studies in adults and animal models (Thayer, 2009; Rosas-Ballina & Tracey, 2009) provide evidence to support that vagal activity has an inhibitory function in inflammatory pathways. Tonic control of cytokine production and leukocyte trafficking by the vagus is an important mechanism in adjusting to stress load (allostasis). In addition, there may be a direct effect on immune cells residing in or recruited to innervated bowel tissue. In contrast to no vagal stimulation, vagal nerve stimulation increases gut motility and reduces inflammatory cell recruitment by inactivating macrophages in the intestinal wall close to cholinergic terminals. Epithelial gut barrier integrity is affected by cholinergic signaling and pro-inflammatory cytokine release. It may be possible for intestinal bacteria to enter the blood stream when the gut mucosal barrier is breached.

In premature infants the immature gut is thought to respond to injury with excessive inflammation. An imbalance of inflammatory effects may contribute to damage as recruited inflammatory leukocytes release oxidants and proteases damaging the intestinal barrier and advancing a cascade of pro-inflammatory tissue responses (Lin, Nasr, Stoll, 2008). We speculate that these effects are enhanced when there is low parasympathetic tone, or low HF. As such, low HF power in the first week of life in otherwise healthy premature infants may be an important marker of vulnerability for later NEC or Sepsis. As a biomarker of immune/regulatory and gut function, this has implication for prevention and early detection of NEC and late-onset sepsis.

While we have shown and described certain present preferred embodiments of our invention and have illustrated certain present preferred methods of using the same, it is to be distinctly understood that the invention is not limited thereto but may be otherwise variously embodied and practiced within the scope of the following claims.

Patents, patent applications, publications, scientific articles, books, web sites, and other documents and materials referenced or mentioned herein are indicative of the levels of skill of those skilled in the art to which the inventions pertain, as of the date each publication was written, and all are incorporated by reference as if fully rewritten herein. Inclusion of a document in this specification is not an admission that the document represents prior invention or is prior art for any purpose.

We claim:

1. A method for determining that a patient is at an elevated risk for developing necrotizing enterocolitis, comprising:
   monitoring a patient's heart rate via electrocardiogram measurements and determining heart rate variability, said heart rate variability having a high frequency component;
   recording the high frequency component of the patient's heart rate via a computer;
   converting the high frequency component to a HF power score via the computer, wherein the HF power score is a measure of power based on the frequency of the high frequency component;
   monitoring the patient's respiratory rate via thoracic impedance measurements and recording an average respiratory rate of the patient via the computer, the average respiratory rate including a mean respiratory rate and two standard deviations about the mean respiratory rate;
   converting the average respiratory rate to a frequency band via the computer and defining the frequency band as a high frequency bandwidth (HF bandwidth);
   setting a HF power cut off value that lies within the HF bandwidth via the computer, wherein the HP power cut off value is 8 $msec^2$;
   comparing, via the computer, the HF power score to the HF power cut off value;
   determining, via the computer, that the patient has an elevated risk for developing necrotizing enterocolitis when the HF power score of the patient is less than the HF power cut off value.

2. The method of claim 1, wherein said HF power score is obtained by sampling at a frequency between 800 and 1200 samples/sec.

3. The method of claim 2, wherein said HF power score is determined by sampling at a frequency of 1000 samples/sec.

4. The method of claim 1, wherein the HF power score is validated by taking multiple 120 second epochs of data for analysis.

5. The method of claim 1, wherein the HF bandwidth is within the range of 0.3 to 1.3 Hz.

6. The method of claim 1, wherein the HF power score is obtained by sampling at a frequency of 1000 samples/second, and is validated by taking multiple 120 second epochs of data, excluding clear outliers.

7. The method of claim 1, wherein the monitoring of the patient's heart rate and the monitoring of the patient's respiratory rate occurs while the patient is at rest, undisturbed by procedures, in light sleep, and post prandial.

8. The method of claim 1, wherein the elevated risk is determined when the HF power score of the patient is less than 5 msec.

9. The method of claim 1, wherein the patient is a preterm neonate with a mass less than or equal to 3000 g.

10. The method of claim 1, comprising monitoring of the patient's heart rate and the monitoring of the patient's respiratory rate between 5 and 8 days after birth of the patient, and repeating the monitoring steps at intervals thereafter.

11. The method of claim 1, wherein the elevated risk is indicative of development of necrotizing enterocolitis within 12 hours to 30 days of a determination of risk.

12. A method for treating a patient for necrotizing enterocolitis, comprising:
   determining that the patient has an elevated risk for developing necrotizing enterocolitis using the method of claim 1;
   administering to the patient a treatment effective to lessen or eliminate at least one of necrotizing enterocolitis or the elevated risk of developing necrotizing enterocolitis.

13. The method of claim 12, wherein said treatment includes administering to the patient an effective amount of antibiotics.

14. A method for determining that a patient is at an elevated risk for developing necrotizing enterocolitis, comprising:
   monitoring a patient's heart rate via electrocardiogram measurements and determining heart rate variability, said heart rate variability having a high frequency component;
   recording the high frequency component of the patient's heart rate and converting the high frequency component to a power measurement via a computer;
   monitoring the patient's breathing rate via thoracic impedance measurements and recording, via the computer, an upper breathing rate limit and a lower breathing rate limit;
   dividing, via the computer, the upper breathing rate limit by 60 and the lower breathing rate limit by 60, generating a high frequency range;
   when the power measurement of the high frequency component falls within the high frequency range, determining, via the computer, that the patient does not have an elevated risk for developing necrotizing enterocolitis; and
   when the power measurement of the high frequency component does not fall within the high frequency range, determining, via the computer, that the patient does have an elevated risk for developing necrotizing enterocolitis.

* * * * *